(12) United States Patent
Lemaster (10) Patent No.: US 9,400,239 B2
(45) Date of Patent: Jul. 26, 2016

(54) METHODS, SYSTEMS, AND COMPUTER READABLE MEDIA FOR TESTING CUTTING BLADE INTEGRITY

(71) Applicant: North Carolina State University, Raleigh, NC (US)

(72) Inventor: Richard Len Lemaster, Apex, NC (US)

(73) Assignee: North Carolina State University, Raleigh, NC (US)

( * ) Notice: Subject to any disclaimer, the term of this patent is extended or adjusted under 35 U.S.C. 154(b) by 412 days.

(21) Appl. No.: 13/954,493

(22) Filed: Jul. 30, 2013

(65) Prior Publication Data

US 2014/0026673 A1   Jan. 30, 2014

Related U.S. Application Data

(60) Provisional application No. 61/677,456, filed on Jul. 30, 2012.

(51) Int. Cl.
*G01N 3/58* (2006.01)

(52) U.S. Cl.
CPC .......... *G01N 3/58* (2013.01); *G01N 2203/0055* (2013.01); *G01N 2203/0057* (2013.01)

(58) Field of Classification Search
CPC .............. G01N 2203/0055; G01N 2203/0057; G01N 3/58; G01N 2203/00; G01N 3/04; G01N 3/32; G01N 3/34; G01N 3/38; G01N 19/06; G01N 19/08; G01N 22/02; G01N 29/041; G01N 29/045; G01N 29/07; G01N 29/11; G01N 29/12; G01N 29/221; G01N 29/223; G01N 29/225; G01N 29/227; G01N 2203/0001; G01N 2203/0003; G01N 2203/0005; G01N 2203/001; G01N 2203/0032; G01N 2203/0039; G01N 2203/006; G01N 2203/0062; G01N 2203/04
See application file for complete search history.

(56) References Cited

U.S. PATENT DOCUMENTS

| | | | | |
|---|---|---|---|---|
| 4,027,531 A * | 6/1977 | Dawson | ................ | B23D 63/18 73/854 |
| 5,115,681 A * | 5/1992 | Bouheraoua | ........... | G01N 29/07 73/643 |
| 6,192,759 B1 * | 2/2001 | Schoess | ................ | G01H 1/003 73/583 |
| 6,742,403 B2 * | 6/2004 | Thomas | ................ | B25B 1/2405 73/862.21 |

FOREIGN PATENT DOCUMENTS

DE             4208330 A1 *  9/1993   ............ G01M 99/00

OTHER PUBLICATIONS

Vary, "The Acousto-Ultrasonic Approach," NASA Technical Memorandum 89843, pp. 1-30 (Jul. 12-15, 1987).

* cited by examiner

*Primary Examiner* — Daniel S Larkin
*Assistant Examiner* — Jamar Ray
(74) *Attorney, Agent, or Firm* — Jenkins, Wilson, Taylor & Hunt, P.A.

(57) ABSTRACT

A system for evaluating integrity of a cutting blade includes at least one stress wave generator for generating at least one stress wave in a cutting blade under test. A sensor detects a signal generated by the at least one stress wave. An integrity analyzer coupled to the sensor determines an indication of integrity of the cutting blade based on at least one characteristic of the signal.

21 Claims, 9 Drawing Sheets

METHODS, SYSTEMS, AND COMPUTER READABLE MEDIA FOR TESTING CUTTING BLADE INTEGRITY

PRIORITY CLAIM

This application claims the benefit of U.S. Provisional Patent Application Ser. No. 61/677,456, filed Jul. 30, 2012; the disclosure of which is incorporated herein by reference in its entirety.

GOVERNMENT INTEREST

This invention was made with government support under Grant Nos. 98-34158-5872 and 2010-34158-20777 awarded by USDA/NIFA. The government has certain rights in the invention.

TECHNICAL FIELD

The subject matter described herein relates to testing cutting tools. More particularly, the subject matter described herein relates to methods, systems, and computer readable media for testing cutting blade integrity.

BACKGROUND

Cutting instruments, such as saws, have blades that rotate, reciprocate, or oscillate at high speeds. Some blades include tips that are brazed onto teeth, which are part of the main blade body. In use, a blade can lose one or more of the tips. Because blades are expensive, rather than discarding blades that have lost one or more tips, the blades are often retipped by brazing new tips onto the saw body to replace the damaged or missing tips. Used blade tips can also be resharpened by grinding the tips.

Because blades operate at high speeds, it is desirable to test the integrity of blades before putting the blades into operation, either after initial manufacturing or after retipping or resharpening. Visual inspection may detect large imperfections in cutting blades. However, visual inspection may fail to detect some imperfections in the cutting blade, such as microcracks or other imperfections that are not visible without magnification. Even with magnification and the use of fluorescent dye, microcracks may not be detectable. Microcracks may be caused by excessive heat in the brazing process. Insufficient heat or insufficient flux may also cause poor or weak braze joints. Currently, there is no known standard method for testing cutting blade integrity.

Accordingly, there exists a need for methods, systems, and computer readable media for testing cutting instrument integrity.

SUMMARY

A system for evaluating integrity of a cutting blade includes at least one stress wave generator for generating at least one stress wave in a cutting blade under test. A sensor detects a signal generated by the at least one stress wave. An integrity analyzer coupled to the sensor determines an indication of integrity of the cutting blade based on at least one characteristic of the signal.

The subject matter described herein can be implemented in software in combination with hardware and/or firmware. For example, the subject matter described herein can be implemented in software executed by a processor. In one exemplary implementation, the subject matter described herein can be implemented using a non-transitory computer readable medium having stored thereon executable instructions that when executed by the processor of a computer control the processor to perform steps. Exemplary non-transitory computer readable media suitable for implementing the subject matter described herein include chip memory devices or disk memory devices accessible by a processor, programmable logic devices, and application specific integrated circuits. In addition, a computer readable medium that implements the subject matter described herein may be located on a single computing platform or may be distributed across plural computing platforms.

BRIEF DESCRIPTION OF THE DRAWINGS

The subject matter described herein will now be explained with reference to the accompanying drawings of which.

DETAILED DESCRIPTION

Figure 1:
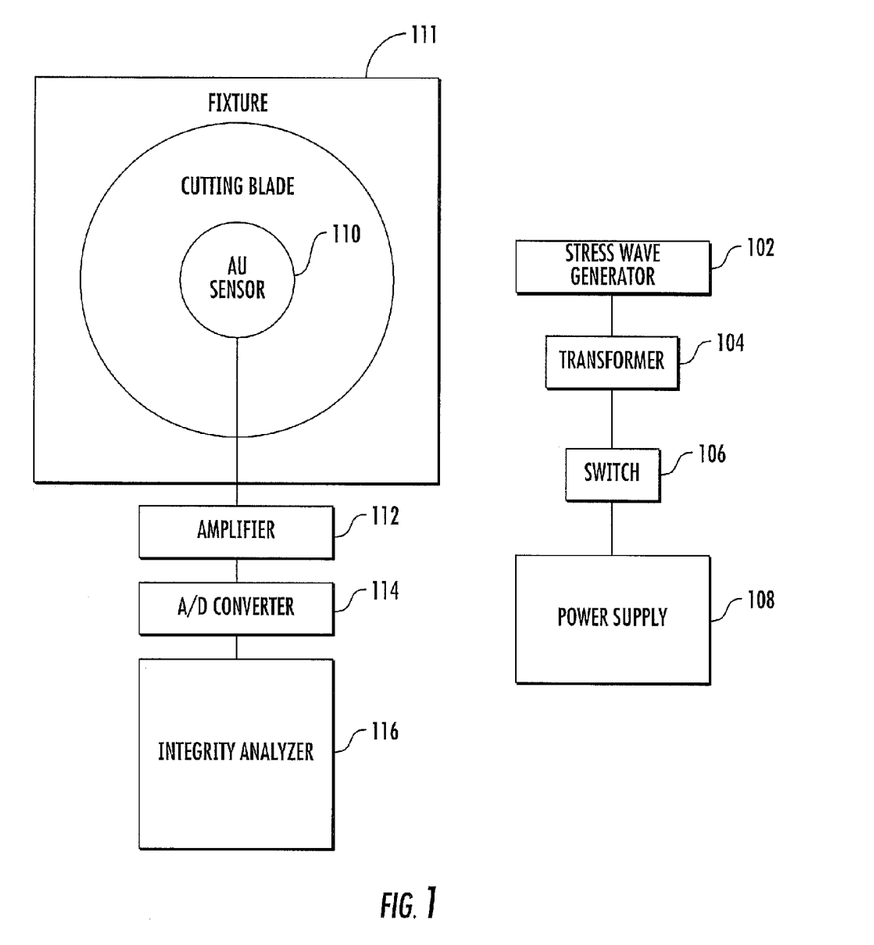
FIG. 1 is a block diagram of a system for testing cutting blade integrity according to an embodiment of the subject matter described herein.

FIG. 1 is a block diagram of a system for testing cutting blade integrity according to an embodiment of the subject matter described herein. Referring to FIG. 1, a cutting blade 100 is shown schematically as a circle. Cutting blade 100 may be any suitable instrument for which it is desirable to test integrity. In one example, cutting blade 100 may be a circular saw blade. In another example, cutting blade 100 may be a non-circular saw blade, such as a planer blade.

As will be described in detail below, cutting blades, such as cutting blade 100, may include tips that are connected to the blade body using braze joints. It is desirable to test the integrity of the braze joints. Accordingly, a stress wave generator 102 may be used to generate stress waves in the cutting blade. In one example, stress wave generator 102 comprises an electrode that generates a spark, and the spark creates the stress wave in cutting blade 100. In other examples, stress wave generator 102 may be a laser or a microhammer. In examples where stress wave generator 102 is an electrode, a transformer 104, a switch 106, and a power supply 108 may be used to generate the voltage necessary to achieve the spark. Transformer 104 may be a step up transformer with a turn ratio sufficient to generate the necessary break down voltage for generating a spark when the electrode is at a desired distance from cutting blade 100. In one example, transformer 104 comprises an ignition coil, similar to that used in an ignition system of an automobile. Switch 106 may be any suitable electrical, mechanical, or electro-mechanical switch for making and breaking the connection between power supply 108 and transformer 104. Power supply 108 may be any suitable power supply for supplying a voltage to the primary side of transformer 104. In one example, power supply 108 comprises a 12 Volt DC power supply.

In order to determine a measure of integrity of cutting blade 100, a sensor 110 is coupled to cutting blade 100. In one exemplary setup, sensor 110 comprises a contact acousto-ultrasonic (AU) sensor, which is placed on a magnet, and the magnet is attached to cutting blade 100 or to a fixture 111 to which cutting blade 100 is attached. In another example, sensor 110 may be an undamped acoustic emission sensor or a piezoelectric sensor. If a laser is used to generate the stress wave in cutting blade 100, sensor 110 may be a laser interferometer. In yet another alternative arrangement, a spark may be used to generate the stress wave in cutting blade 100, and sensor 110 may be a laser interferometer for measuring one or more characteristics of the stress wave.

AU sensor 110 detects an acousto-ultrasonic signal generated by the stress wave. An amplifier 112 may be included to amplify the signal output from AU sensor 110. An analog to digital (A/D) converter 114 converts the amplified signal into digital format that is input into a computer. The interface with the computer may be a USB interface or other suitable interface through which signal data can be passed. In addition, amplifier 112, A/D converter, 114, and at least some signal extraction circuitry may be integrated in a single unit that processes the signal before inputting the signal into a computer. An integrity analyzer 116 analyzes the digitized signal to determine a metric of blade integrity. In one example, integrity analyzer 116 compares a signal from a stress wave generated by origination of a stress wave on a tip of cutting blade 100 to a signal generated by origination of a stress wave of a region of cutting blade 100 adjacent to a tip. Based on the results of the comparison, integrity analyzer 116 may output an indication of cutting blade integrity.

Fixture 111 may be included for holding cutting blade 100. In one example, fixture 111 comprises a stationary structure and stress wave generator 102 is movable with respect to fixture 111. In another example, fixture 111 may be movable to allow movement of cutting blade 100 relative to stress wave generator 102. For example, fixture 111 may allow rotation of cutting blade 100 relative to stress wave generator 102 or movement in the X and Y directions in a plane parallel to a plane of cutting blade 100. Fixture 111 may also allow for cutting blades with variable size central apertures. In one implementation, fixture 111 may be a conic structure for holding cutting blades of different inner aperture or arbor hole diameters.

In the example illustrated in FIG. 1, a single stress wave generator is illustrated. However, the subject matter described herein is not limited to using a single stress wave generator. Multiple stress wave generators located at different locations relative to cutting blade 100 may be used to generate stress waves on cutting blade 100 without departing from the scope of the subject matter described herein. In addition, stress wave generator 102 may be mounted on a movable structure, such as an arm having a joint, to allow positioning of stress wave generator 102 relative to cutting blade 100.

In one implementation, the system illustrated in FIG. 1 may be a bench testing unit suitable for use in manufacturing or cutting blade retipping operations. In another example the system illustrated in FIG. 1 may be implemented as a hand-held unit where stress wave generator 102 and sensor 110 are located in the hand-held unit.

Figure 2A:
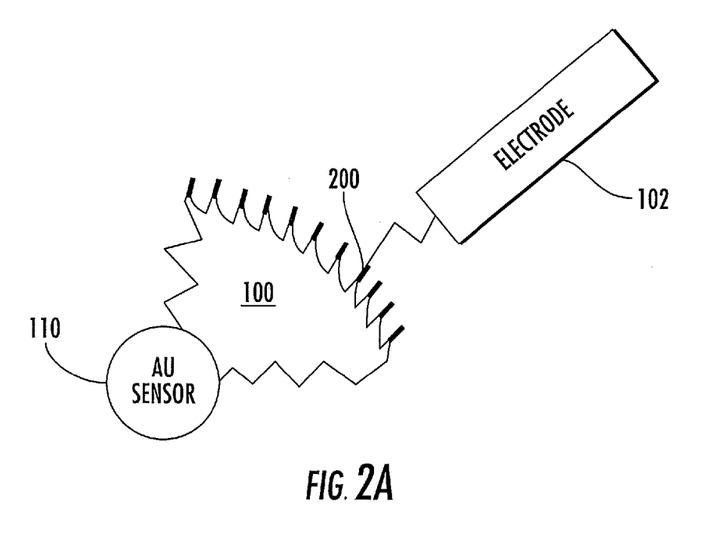
FIGS. 2A and 2B are close up views of a method for generating a stress wave and a cutting blade under test according to an embodiment of the subject matter described herein.
Figure 2B:
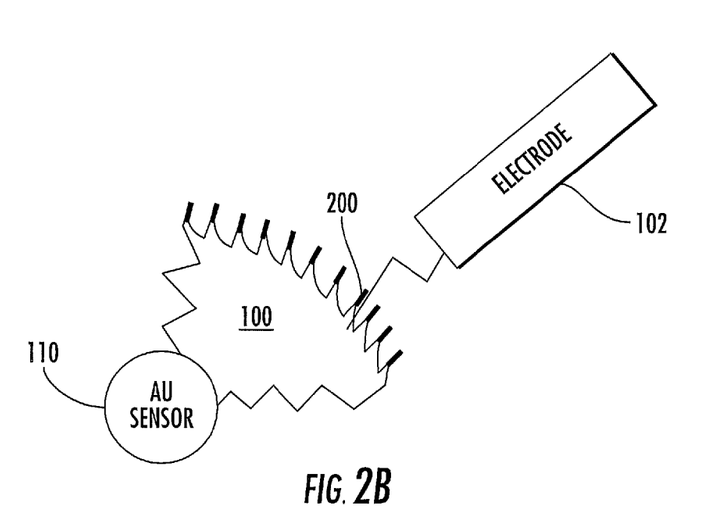

As stated above, the system illustrated in FIG. 1 may be used to generate an indication of cutting tool integrity. FIGS. 2A and 2B illustrate an exemplary method for generating a stress wave in cutting tool 100 and determining the measure of cutting tool integrity. In FIG. 2A, stress wave generator 102 comprises an electrode that applies a spark to a tip 200 of cutting tool 100. In FIG. 2B, electrode 102 applies a spark to a region of cutting tool 100 adjacent to tip 200. AU sensor 110 may receive signals corresponding to the stress waves generated by the electrode in FIGS. 2A and 2B. In one example, the frequency components in a signal for a braze joint being tested may be compared with the frequency components of a reference signal. The relative lack of frequency components in between the signal waveforms may indicate the presence of a discontinuity, such as a microcrack. In another example, a relative decrease in signal amplitude may indicate the presence of a microcrack or other defect. In yet another example, a signal that decays more rapidly than a reference signal may indicate the presence of an imperfection. These or other parameters may be used together and in combination with other parameters to detect the presence of an imperfection, such as a bad braze joint. In one example, signal parameters may be averaged, and the average of the parameters may indicate the presence of a bad braze joint. Accordingly, by analyzing the frequency components, amplitude, decay rates, and/or other parameters of the resulting AU waveform or waveforms, integrity analyzer 116 may determine the presence of a microcrack or other imperfection in a cutting blade.

In one example, the test procedure consists of sending a stress wave through the saw body just behind the saw tooth and then another stress wave through the saw tooth and the saw body. Features of each waveform are extracted and analyzed. These can include but not limited to the energy of the waveform, the RMS (root mean square) of the waveform, the average frequency, the centroid frequency, the rise time, and the waveform duration to name a few.

A ratio is then established between the waveform feature for the stress wave going through the tooth and saw body with the same waveform feature for the stress wave going through just the saw body behind the saw tooth. This is repeated for all the teeth on the saw and then compared with the values obtained from a saw known to be of good quality.

Figure 3A:
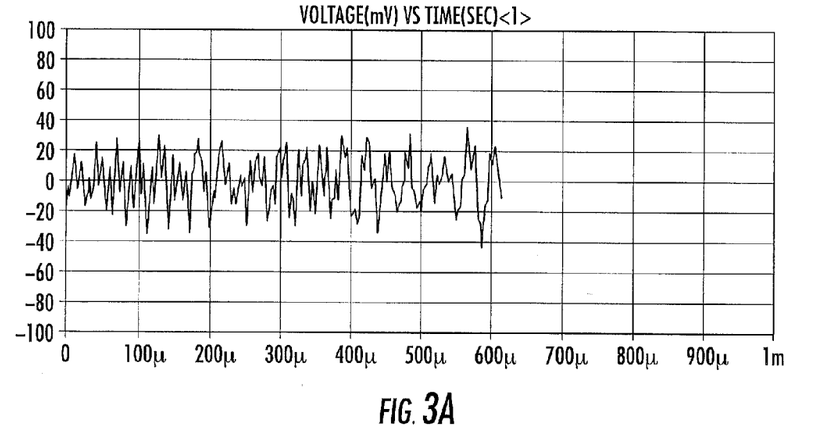
FIG. 3A is a graph of a waveform of a stress wave going through the shoulder of a saw blade behind a tooth.
Figure 3B:
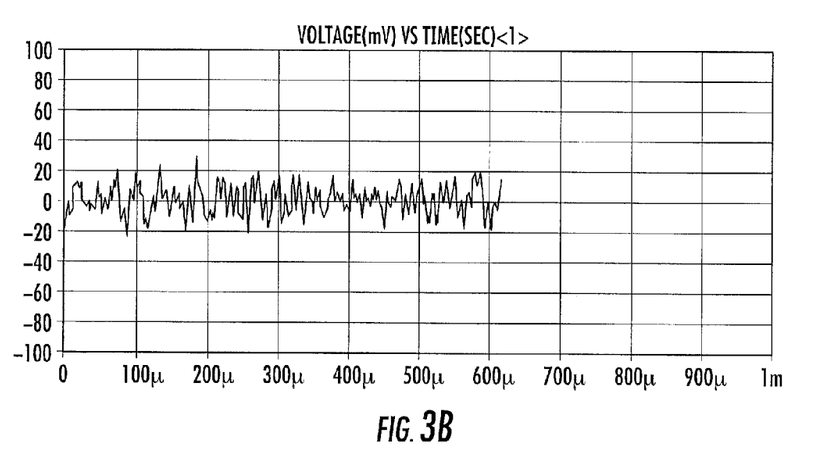
FIG. 3B is a graph of a waveform of a stress wave going through a tooth that did not use flux when brazed onto a saw body.

FIGS. 3A and 3B show the two waveforms (saw body and tooth/saw body) for a saw whose teeth were brazed to the saw body without flux and the ratio of the energy of the waveform.

Figure 3C:
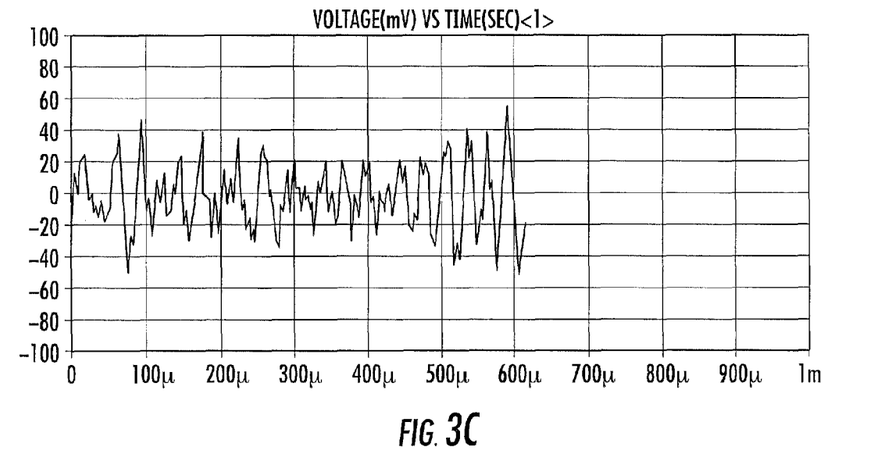
FIG. 3C is a graph of a waveform of a stress wave going through shoulder of saw blade behind tooth on good blade.
Figure 3D:
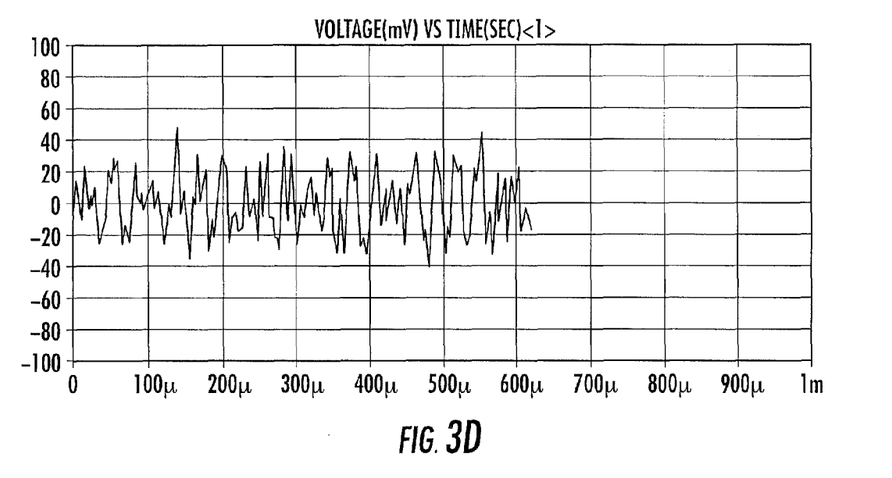
FIG. 3D is a waveform of a stress wave going through a tooth and a saw body for "good" blade.

FIGS. 3C and 3D show the waveform for a "good" saw blade whose teeth were applied with the recommended flux. As can be seen, the waveform of the stress wave going through just the saw body is similar but not identical for the two saw blades. However, the energy ratio shows that there is less difference between the waveform energy between the tooth/saw body path and just the saw body path for a "good" blade when compared with the blade that did not use flux in the brazing operation.

These types of ratios reduce the effect of coupling differences of the sensor between the saw bodies as well as the difference between positions of the teeth around the saw body and how close a tooth is to a slot or hole in the saw body. The energy ratio for the two waveforms in FIGS. 3A and 3B may be calculated as follows:

$$\text{ENERGY RATIO} = \frac{(\text{tooth/saw body})}{\text{Saw body}} \times 100 = 28$$

where the numerator "(tooth/saw body)" is the energy in the waveform that traveled through the tooth and the saw body and the denominator "Saw Body" is the energy in the waveform that traveled through the saw body.

The following energy ratio may be calculated for the waveforms in FIGS. 3C and 3D:

$$\text{ENERGY RATIO} = \frac{(\text{tooth/saw body})}{\text{Saw body}} \times 100 = 75$$

where the terms have the same meaning as the energy ratio for FIGS. 3A and 3B. It can be seen that the energy ratio for the good blade (FIGS. 3C and 3D) is higher than the energy ratio for the bad blade (FIGS. 3A and 3B). Thus, by comparing an energy ratio of a blade under test to an energy ratio for a known good blade, an indication of a defect in the blade under test can be determined.

Figure 4:
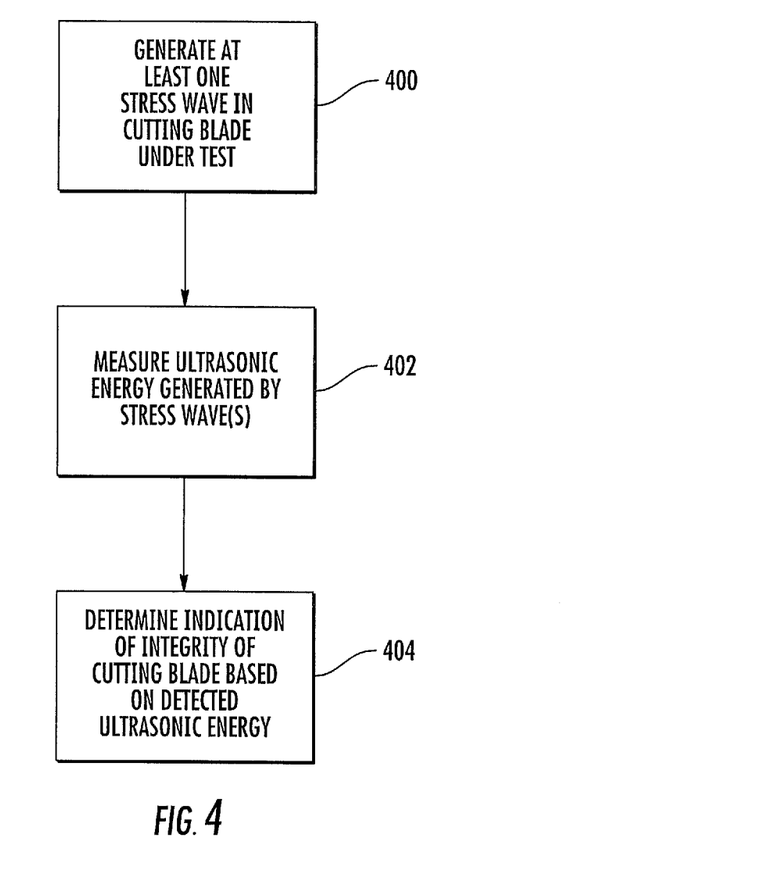
FIG. 4 is a flow chart of an exemplary process for determining a metric of cutting tool integrity according to an embodiment of the subject matter described herein.

FIG. 4 is a flow chart illustrating an exemplary method for determining a metric of cutting tool integrity according to an embodiment of the subject matter described herein. Referring to FIG. 4, in step 400, at least one stress wave is generated in a cutting tool under test. For example, stress wave generator 102 may generate a stress wave in cutting tool 100 using a spark, a laser, or mechanical means, such as a hammer or solenoid. In step 402, a signal generated by the stress wave is detected. For example, AU sensor 110 may detect an acousto-ultrasonic waveform generated by the stress wave in cutting blade 100. In step 404, an indication of the integrity of the cutting blade is determined based on characteristics of the signal. For example, integrity analyzer 116 may analyze frequency components, amplitude, and/or decay rate of the resulting waveform or waveforms measured by sensor 110 to determine the presence of an imperfection in a cutting blade.

Figure 5:
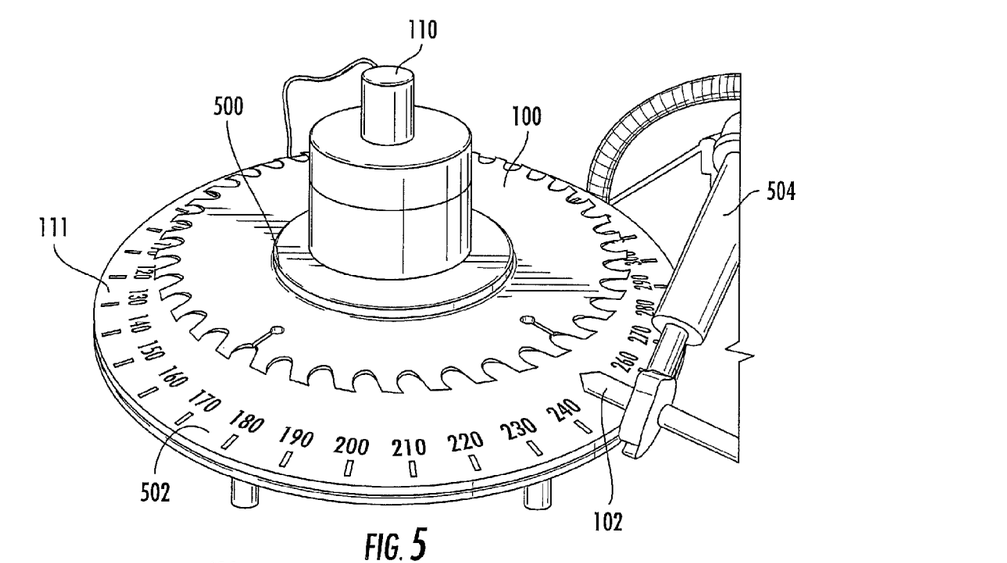
FIG. 5 is a diagram illustrating a cutting blade mounted to a rotary fixture according to an embodiment of the subject matter described herein.

FIG. 5 is a diagram illustrating an example where cutting blade 100 is a saw blade and fixture 111 is a rotary table to allow rotation of the saw blade relative to electrode 102. In FIG. 5, fixture 111 includes a cylindrical or conical protrusion 500 that extends through the central aperture in cutting blade 100. Protrusion 500 rotates relative to base portion 502 so that blade 110 can be tested at different circumferential positions. Electrode 102 is mounted on a moveable arm 504 that allows the spark gap for the electrode to be adjusted.

Figure 6:
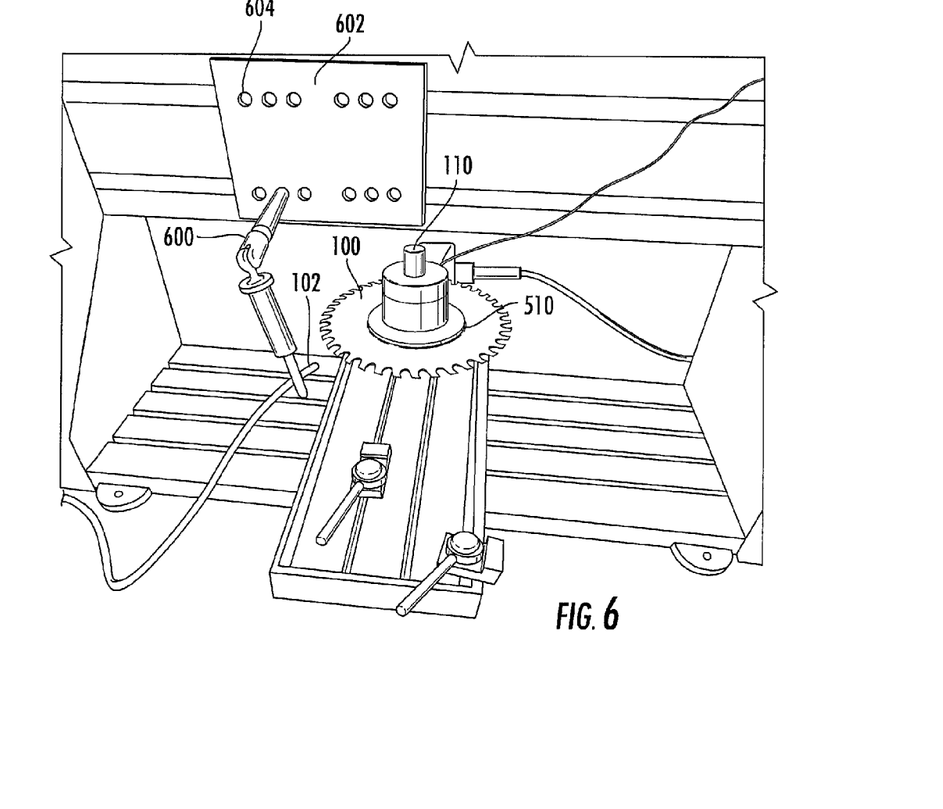
FIG. 6 is a diagram of a fixture where the cutting blade is stationary and the electrode is mounted on the jointed arm that is movable relative to the cutting blade.

FIG. 6 is another diagram where cutting blade 100 is stationary and electrode 102 is mounted on a jointed arm that is movable relative to the saw blade. In FIG. 6, jointed arm 600 allows electrode 102 to be moved radially with respect to cutting blade 110. In addition, a plate 602 mounted above saw blade 100 includes aperture 604 that allow jointed arm 600 to be moved different positions along the circumference of cutting blade 100. Plate 602 may be stationary or moveable.

Figure 7:
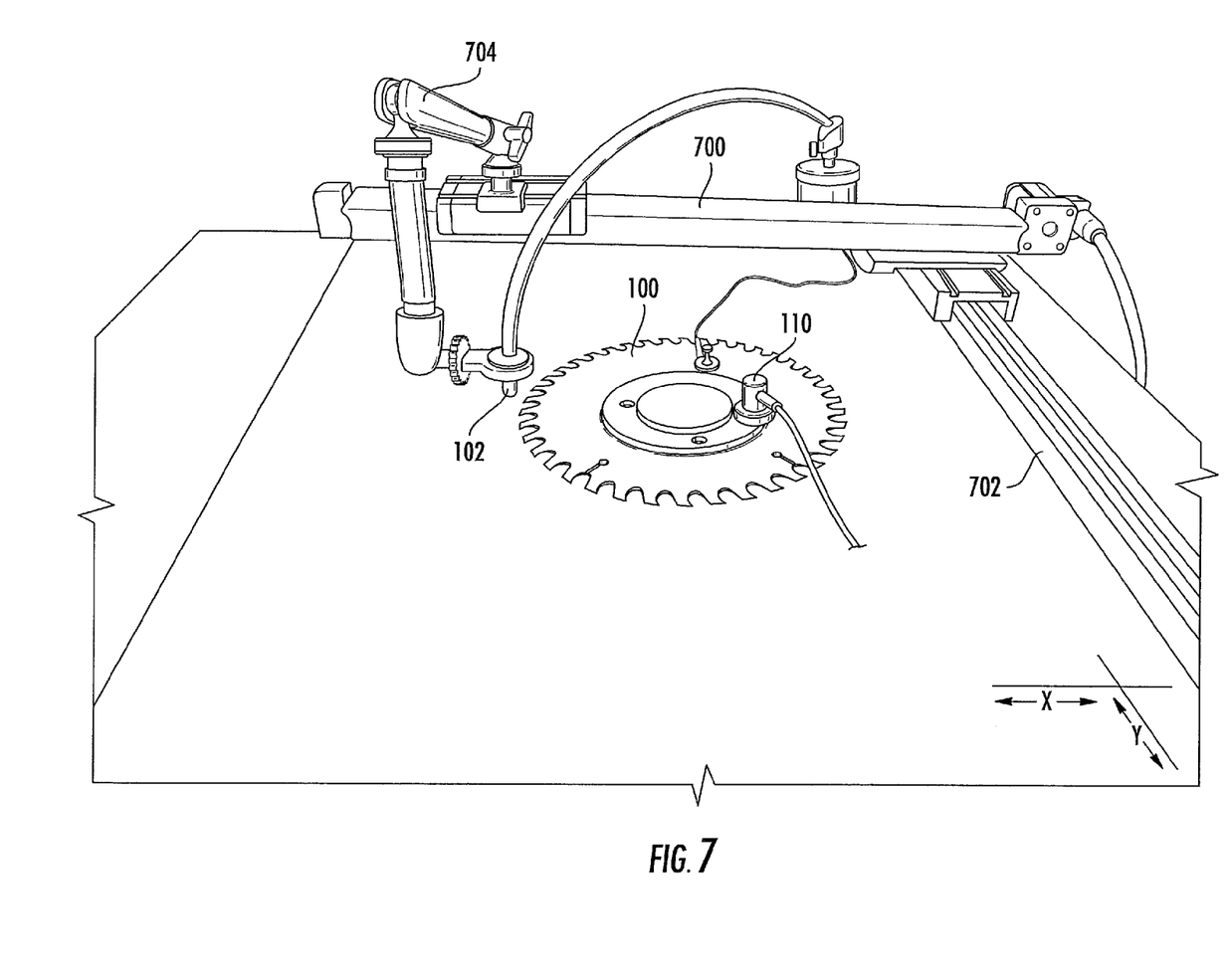
FIG. 7 is a diagram of a cutting blade and a fixture where the blade is stationary and the electrode is mounted on a structure that is movable in X and Y directions in a plane parallel to the plane of the cutting blade according to an embodiment of the subject matter described herein.

FIG. 7 is another example of a setup where the saw blade is stationary and the electrode can be mounted on a structure that is movable in X and Y directions in a plane parallel to the plane of the cutting blade. In FIG. 7, the structure or fixture on which the electrode can be mounted comprises a pair of arms 700 and 702 where one arm 700 is moveably mounted to the other arm 702 and extends in the direction that is orthogonal to the other arm 702. Electrode 102 is mounted on a jointed arm 704 that is attached to upper arm 700. Jointed arm 704 slides in the X direction across upper arm 700. Arm 700 slides in the Y direction across arm 702. Because arm 704 slides in the X direction and arm 700 slides in the Y direction, electrode 102 can be placed at virtually any location to generate a spark and a stress corresponding stress wave in cutting blade 100.

Figure 8:
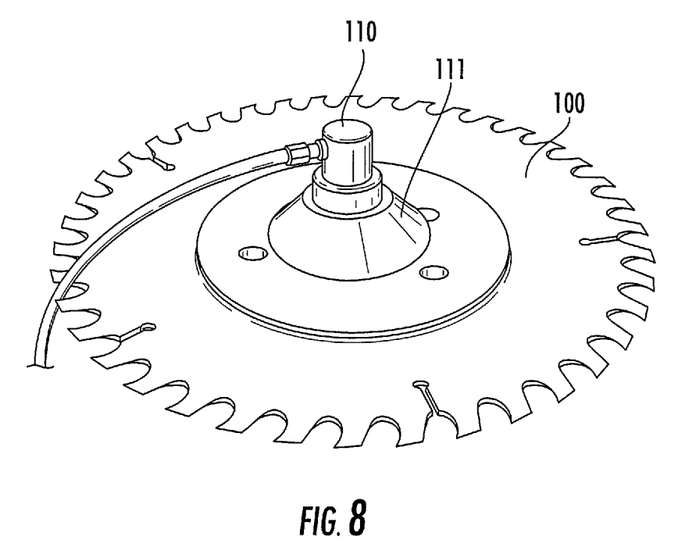
FIG. 8 is a diagram of a fixture comprising a conic structure for holding cutting blades with different arbor hole diameters according to an embodiment of the subject matter described herein.

FIG. 8 is diagram of a cutting blade 100 mounted on a fixture 111 that comprises a conic structure that is configured to receive cutting blades of different diameters. Note that in FIG. 8, sensor 110 is mounted to conic structure 111 which is in physical contact with cutting blade 100. The above-described process of generating a spark on one of the carbide tips, measuring the associated stress wave using the sensor, generating a second spark on the saw body adjacent to the tip, measuring the stress wave, and comparing the stress waves works with the embodiment illustrated in FIG. 8. Because the reference signal generated by the stress wave originating from the spark adjacent to the tip must travel through essentially the same path as the stress wave originating from the spark on the tip, comparing the resulting waveforms can identify discontinuities in the tip or between the tip and the cutting blade body caused by microcracks or other defects.

Figure 9:
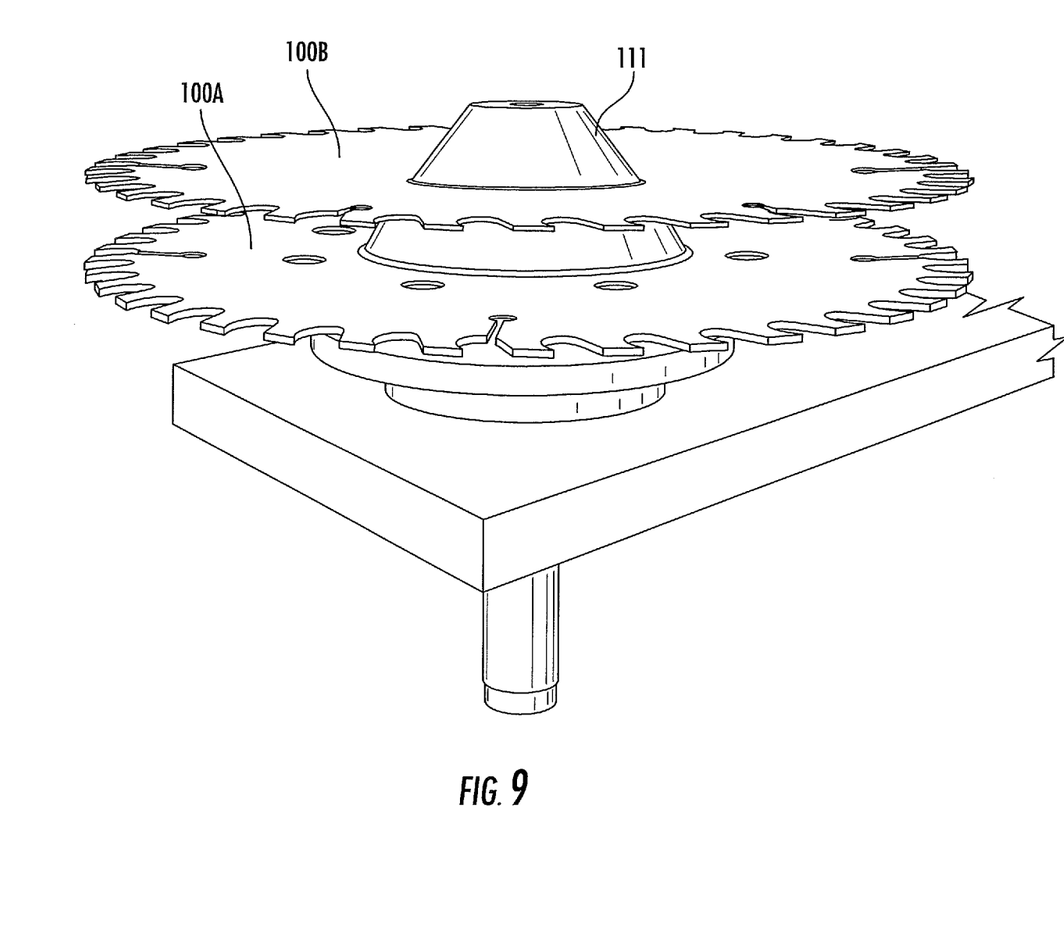
FIG. 9 is a diagram of a fixture for holding cutting blades with different arbor hold diameters according to an embodiment of the subject matter described herein.

FIG. 9 is a diagram where fixture 111 comprises a conical saw blade holder that is an alternative to using arbor adaptors to center the saw blade on the testing unit. The metal cone will hold saw blades with various arbor hole diameters. The cone will be adjusted vertically and rise from beneath the testing table so that the saw blade will be centered and held at the proper height from the table. FIG. 9 illustrates fixture 111 holding saw blades 100A and 100B with different arbor hole diameters.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A system for evaluating integrity of a cutting blade, the system comprising: at least one stress wave generator for generating at least one stress wave in a cutting blade under test; a sensor for detecting a signal generated by the at least one stress wave; and an integrity analyzer coupled to the sensor for determining an indication of integrity of the cutting blade based at least one characteristic of the signal, wherein the integrity analyzer is configured to compare an energy ratio for the cutting blade under test to an energy ratio for a reference blade to determine the indication of integrity.

2. The system of claim 1 wherein the at least one stress wave generator comprises at least one electrode for applying at least one spark to the cutting blade under test.

3. The system of claim 2 wherein the at least one electrode comprises a single electrode.

4. The system of claim 2 wherein the at least one electrode comprises a plurality of electrodes for generating sparks at different locations of the cutting blade.

5. The system of claim 1 wherein the at least one stress wave generator comprises a laser or a microhammer.

6. The system of claim 1 comprising a fixture for holding the cutting blade under test.

7. The system of claim 6 wherein the fixture includes an adapter for holding cutting blades with differing central aperture diameters.

8. The system of claim 7 wherein the adapter comprises a conic structure.

9. The system of claim 6 wherein the fixture is movable so that the cutting blade can be moved with respect to the at least one stress wave generator.

10. The system of claim 9 wherein the at least one stress wave generator is stationary and wherein the fixture is movable in a plane parallel to a plane of the cutting blade.

11. The system of claim 9 wherein the fixture allows rotation of the cutting blade with respect to the at least one stress wave generator.

12. The system of claim 6 wherein the fixture is stationary and the at least one stress wave generator is movable with respect to the cutting blade.

13. The system of claim 12 comprising a movable arm and wherein the at least one stress wave generator is mounted on the movable arm.

14. The system of claim 13 wherein the movable arm includes at least one joint for facilitating placement of the at least one stress wave generator.

15. The system of claim 1 wherein the integrity analyzer determines the indication of integrity of the cutting blade by analyzing at least one of: frequency components, amplitude, and decay rate of the signal.

16. The system of claim 15 wherein analyzing the frequency components includes determining the presence or absence of a discontinuity in a region of the cutting blade.

17. The system of claim 16 wherein the region of the cutting blade comprises a braze joint that holds a tip to a main body of the cutting blade.

18. The system of claim 1 comprising a portable housing, wherein the at least one stress wave generator, the sensor, and the integrity analyzer are located in the housing.

19. The system of claim 18 wherein the housing comprises a hand-held unit.

20. The system of claim 1 wherein the sensor comprises an acousto-ultrasonic (AU) sensor or an acoustic emission sensor.

21. The system of claim 1 wherein the sensor comprises a laser interferometer.

* * * * *